US008916351B2

(12) United States Patent
Murakami

(10) Patent No.: US 8,916,351 B2
(45) Date of Patent: Dec. 23, 2014

(54) PRIMER GENERATION ROLLING CIRCLE AMPLIFICATION

(75) Inventor: Taku Murakami, Aliso Viejo, CA (US)

(73) Assignees: Hitachi Chemical Co., Ltd., Tokyo (JP); Hitachi Chemical Research Center, Inc., Irvine, CA (US)

(*) Notice: Subject to any disclaimer, the term of this patent is extended or adjusted under 35 U.S.C. 154(b) by 1918 days.

(21) Appl. No.: 11/813,142

(22) PCT Filed: Jan. 4, 2006

(86) PCT No.: PCT/US2006/000086
§ 371 (c)(1),
(2), (4) Date: Mar. 3, 2009

(87) PCT Pub. No.: WO2006/074162
PCT Pub. Date: Jul. 13, 2006

(65) Prior Publication Data
US 2009/0233277 A1  Sep. 17, 2009

Related U.S. Application Data

(60) Provisional application No. 60/641,255, filed on Jan. 4, 2005, provisional application No. 60/699,340, filed on Jul. 14, 2005.

(51) Int. Cl.
*C12Q 1/68* (2006.01)
*C12P 19/34* (2006.01)

(52) U.S. Cl.
CPC ............... *C12P 19/34* (2013.01); *C12Q 1/6844* (2013.01)
USPC ........................... 435/6.12; 435/6.1; 435/6.11

(58) Field of Classification Search
CPC .. C12Q 1/6806; C12Q 1/6844; C12Q 1/6858; C12Q 1/6865
See application file for complete search history.

(56) References Cited

U.S. PATENT DOCUMENTS 5,770,408 A  6/1998 Sato
5,854,033 A  12/1998 Lizardi
(Continued)

FOREIGN PATENT DOCUMENTS

WO  92/01813  2/1992
WO  99/09216  2/1999
(Continued)

OTHER PUBLICATIONS

Dahl et al., "Circle-to-circle amplification for precise and sensitive DNA analysis," PNAS, Mar. 30, 2004, vol. 101, No. 13, pp. 4548-4553.*

(Continued)

*Primary Examiner* — Young J Kim
(74) *Attorney, Agent, or Firm* — Knobbe Martens Olson & Bear, LLP

(57) ABSTRACT

A method of amplifying a nucleic acid includes combining a first linear primer with a polymerase and a circular probe. The circular probe contains at least one antisense sequence to a second nucleic acid sequence and at least one antisense sequence to the first linear primer. The method also includes producing at least one repeat of an antisense copy of the circular probe by rolling circle amplification. The antisense copy contains at least the second nucleic acid sequence. The method further includes generating more than one second linear primers from each copy of the second nucleic acid sequence; and hybridizing the second linear primers to more than one of the circular probes. A ribbon probe includes a circular probe and a lock probe. The lock probe contains at least a cleavable linker, and the circular probe and the lock probe are unable to dissociate without cleaving the cleavable linker.

14 Claims, 11 Drawing Sheets

(56) References Cited

U.S. PATENT DOCUMENTS 6,221,603 B1 4/2001 Mahtani
6,291,187 B1 9/2001 Kingsmore et al.

FOREIGN PATENT DOCUMENTS

| WO | 99/49079 | 9/1999 |
| WO | 00/04193 | 1/2000 |
| WO | 00/23619 | 4/2000 |

OTHER PUBLICATIONS

Cheng et al, Highly sensitive determination of microRNA using target-primed and branched rolling-circle amplification, Angew. Chem. Int. Ed. Engl., Feb. 13, 2009, vol. 48, pp. 3268-3272.
Dahl et al, Circle-to-circle amplification for precise and sensitive DNA analysis, Proc. Natl. Acad. Sci. USA, Mar. 15, 2004, vol. 101, Issue 13, pp. 4548-4553.
Duck et al, Probe Amplifier System Based on Chimeric Cycling Oligonucleotides, Biotechniques, 1990, vol. 9, Issue 2, pp. 142-147.
Eis et al, an invasive cleavage assay for direct quantitation of specific RNAs, Nature Biotechnology, Jul. 2001, vol. 19, Issue 7, pp. 673-676.
Fire et al., Rolling replication of short DNA circles, Proc. Natl. Acad. Sci USA, May 9, 1995, vol. 92, pp. 4641-4645.
Gullberg, Cytokine detection by antibody-based proximity ligation, Proc. Natl. Acad. Sci. USA, May 21, 2004, vol. 101, Issue 22, pp. 8420-8424.
Lizardi et al., Mutation detection and single-molecule counting using isothermal rolling-circle amplification, Nature America, Jul. 19, 1998, pp. 225-232.
Lyamichev, Polymorphism identification and quantitative detection of genomic DNA by invasive cleavage of oligonucleotide probes, Nature Biotechnology, Mar. 1999, vol. 17, Issue 3, pp. 292-296.
Murakami et al., Sensitive Isothermal Detection of nucleic-acid sequence by primer generation-rolling circle amplification, Nucleic Acids Research, Dec. 23, 2008, vol. 37, Issue 3, pp. e19.
Murakami et al., Nucleic Acid Detection by Primer Generation-rolling Circle Amplification, EPICENTRE Forum Newsletter, Jun. 2009, vol. 16, Issue 2, pp. 7-9.
Nilsson et al., Padlock Probes: Circularizing Oligonucleotides for Localized DNA Detection, Science, Sep. 30, 1994, vol. 265, pp. 2085-2088.
Schweitzer et al., Immunoassays with rolling circle DNA amplification: A versatile platform for ultrasensitive antigen detection, Proc. Natl. Acad. Sci. USA, Aug. 29, 2000, vol. 97, Issue 18, pp. 10113-10119.
Zhang et al, Amplification of target-specific ligation-dependent circular probe, Gene, May 12, 1998, vol. 211, pp. 277-285.
Rector et al., A Sequence-Independent Strategy for Detection and Cloning of Circular DNA Virus Genomes by Using Multiply Primed Rolling-Circle Amplification, Journal of Virology, May 2004, vol. 78, Issue 10, pp. 4993-4998.
Baner et al., Signal amplification of padlock probes by rolling circle replication, Nucleic Acids Research, Nov. 15, 1998, vol. 26, Issue 22, pp. 5073-5078.
Kuhn et al., Rolling-circle amplification under topological constraints, Nucleic Acids Research, Jan. 15, 2002, vol. 30, Issue 2, pp. 574-580.
Liu et al., Rolling Circle DNA Synthesis, J. Am Chem. Soc., Feb. 21, 1996, vol. 118, Issue 7, pp. 1457-1594.
Nilsson et al., Enhanced detection and distinction of RNA by enzymatic probe ligation, Nature Biotechnology, Jul. 2000, vol. 18, Issue 7, pp. 791-793.
Nilsson et al., RNA-templated DNA ligation for transcript analysis, Nucleic Acids Research, Jan. 15, 2001, vol. 29, Issue 2, pp. 578-581.
Wharam et al., Specific detection of DNA and RNA targets using a novel isothermal nucleic acid amplification assay based on the formation of three-way junction structure, Nucleic Acids Research, Dec. 23, 2008, vol. 29, Issue 11, pp. 1-8.
European Patent Office, EP Appl. No. 06717311.2 Office Action, Feb. 16, 2010.
Larsson et al., In situ genotyping individual DNA molecules by target-primed rolling-circle amplification of padlock probes, Nature Methods, Dec. 2004, vol. 1, Issue 3, pp. 227-232.
European Patent Office, Search Report for EP10195226.5, Apr. 11, 2011.
Fredriksson et al., Protein Detection Using Proximity-Dependent DNA Ligation Assays, Nature Biotechnology, May 2002, vol. 20, pp. 473-477.
Kuzuya et al., Selective Activation of Two Sites in RNA by Acridine-Bearing Oligonucleotides for Clipping of Designated RNA Fragments, J. Am. Chem. Soc., Jan. 2004, vol. 126, Issue 5, pp. 1430-1436.
Molloy et al., Cleavage of DNA/RNA Hybrids by Type II Restriction Enzymes, Nucleic Acid Research, May 1980, vol. 8, Issue 13, pp. 2939-2946.
Ueda et al., Open Sandwich ELISA: A novel immunoassay based on the interchain interaction of antibody variable region, Dec. 1996, vol. 14, pp. 1714-1718.

\* cited by examiner

PRIMER GENERATION ROLLING CIRCLE AMPLIFICATION

CROSS REFERENCE TO RELATED APPLICATIONS

This application is the U.S. National Phase under 35 U.S.C. §371 of International Application No. PCT/US2006/000086, filed on Jan. 4, 2006, which claims the benefit of U.S. Provisional Application No. 60/641,255, filed on Jan. 4, 2005 and of U.S. Provisional Application No. 60/699,340, filed Jul. 14, 2005, the entire contents of each of which is incorporated by reference herein.

BACKGROUND OF THE INVENTION

1. Field of the Invention

The present invention, primer generation-rolling circle amplification (PG-RCA), allows the single step detection of nucleic acid sequences such as DNA and RNA sensitively and rapidly. Furthermore, this technology is easily applicable to detection of other biomolecules, such as DNA methylation, single nucleotide polymorphisms (SNP), proteins and post-translational modifications. The invention also relates to a ribbon probe useful in PG-RCA.

2. Description of the Related Art

A variety of nucleic acid sequence detection technologies have been established in recent years for in vitro diagnostics. Several of these technologies are PCR (polymerase chain reaction), LCR (Ligase chain reaction), RCA (rolling circle amplification), NASBA (nucleic acid sequence based amplification) and TMA (transcription mediated amplification). Some of these technologies allow detection of even less than 10 molecules through their exponential amplification mechanism.

In pathogen detection, these amplification technologies are widely utilized to detect contamination by pathogens in a sample by targeting pathogen-specific sequences or genes found in a pathogen's genomic DNA. However, as a single cell contains only a single set of genomic DNA, these nucleic acid amplification-based pathogen assays have only comparable sensitivity to other conventional assays such as enzyme linked immunosorbent assay (ELISA). One solution is to target more abundant pathogen-specific rRNA or mRNA, but many of the nucleic acid amplification reactions utilize DNA polymerase, which cannot polymerize on RNA templates efficiently, therefore RNA targets cannot be directly detected in many of these amplification methods.

Reverse transcription-polymerase chain reaction (RT-PCR) is most widely used to detect target RNA sequence through conversion of RNA sequences to single strand or double strand DNA by reverse transcriptase followed by PCR amplification. However, as RT and PCR need to be conducted separately due to the difference in their reaction conditions, RT-PCR takes a few hours in total to obtain a detectable amount of product and sometimes requires transferring RT product into PCR, which is very tedious when there are many samples.

Ligation-rolling circle amplification is another way to detect target RNA sequence through ligation of the 5' and 3' ends of a padlock probe or linear nucleic acid probe on the target RNA followed by hyperbranched rolling circle amplification (HRCA) to quantitate the circularized padlock probe. However, this method requires at least two reactions, ligation and HRCA, and may require exonuclease treatment to remove uncircularized padlock probes after circularization for an efficient HRCA reaction. Furthermore, DNA ligase-based ligation on an RNA template is known to be less efficient than on a DNA template, therefore small amounts of target RNA may not be detected.

SUMMARY OF THE INVENTION

In an aspect of the present invention, a method of amplifying a nucleic acid is provided which comprises: generating a first nucleic acid primer from a first nucleic acid sequence; combining the first nucleic acid primer with a first polymerase and a first circular nucleic acid probe, wherein the first circular nucleic acid probe contains at least one antisense sequence to a second nucleic acid sequence and at least one antisense sequence to the first nucleic acid primer; producing at least one repeat of a sequence copy of the first circular nucleic acid probe by rolling circle amplification using the first polymerase, wherein the sequence copy contains at least the second nucleic acid sequence; generating a second nucleic acid primer from the second nucleic acid sequence; combining the second nucleic acid primer with a second polymerase and a second circular nucleic acid probe, where the second circular nucleic acid probe contains at least one antisense sequence to the second nucleic acid primer; and producing at least one repeat of a sequence copy of the second circular nucleic acid probe by rolling circle amplification using the second polymerase.

In a further aspect of this method, the first nucleic acid sequence and the second nucleic acid sequence are the same sequence.

In another aspect of the present invention, a method is provided for detecting a molecule that comprises: initiating a first primer generation reaction using the molecule, wherein the first primer generation reaction generates a first nucleic acid primer; combining the first nucleic acid primer with a first polymerase and a first circular nucleic acid probe, wherein the first circular nucleic acid probe contains at least one antisense sequence to a second nucleic acid sequence and at least one antisense sequence to the first nucleic acid primer; producing at least one repeat of a first sequence copy of the first circular nucleic acid probe by rolling circle amplification using the first polymerase, wherein the first sequence copy contains at least a second nucleic acid sequence; generating at least a second nucleic acid primer using the second nucleic acid sequence; combining the second nucleic acid primer with a second polymerase and a second circular nucleic acid probe, wherein the second circular nucleic acid probe contains at least one antisense sequence to the second nucleic acid sequence and at least one antisense sequence to the second primer; producing at least one repeat of a second sequence copy of the second circular nucleic acid probe by rolling circle amplification using the second polymerase, wherein the second sequence copy contains at least the second nucleic acid sequence; repeating, at least once, the generating, combining, and producing steps using the second nucleic acid sequence contained in the second sequence copy; and detecting a product of the second polymerase or the second nucleic acid primer as an indication of the presence of the molecule.

In a further aspect of this method, the first nucleic acid sequence and the second nucleic acid sequence are the same sequence.

In a further aspect, at least two first or second nucleic acid primers are generated from the first or second nucleic acid sequences in the generating steps.

In a further aspect, the first and second nucleic acid primers are generated by at least one of polymerization, cleavage, transcription, and high order nucleic acid structure formation.

In a further aspect, the first and second nucleic acid primers are generated by one of nuclease-based cleavage reaction, strand displacement amplification, cleavage-initiated isothermal amplification, three-way junction isothermal amplification and three-way junction rolling circle reaction.

In a further aspect, the first and second nucleic acid primers are generated by one of nuclease-based cleavage reaction, strand displacement amplification, cleavage-initiated isothermal amplification, three-way junction isothermal amplification, three-way junction rolling circle reaction, binding assay using a nucleic acid labeled recognition agent and proximity assay.

In a further aspect, the molecule detected is selected from the group consisting of methylated DNA and single nucleotide polymorphisms.

In another aspect of the invention, a ribbon probe is provided that comprises a circular nucleic acid probe and a nucleic acid lock probe, wherein: the nucleic acid lock probe contains at least a cleavable linker, and the circular nucleic acid probe and the lock probe are unable to dissociate without cleaving the cleavable linker.

In a further aspect, the circular probe comprises at least a primer generation sequence or an antisense sequence thereto.

In a further aspect, the cleavable linker comprises a nucleic acid, nucleic acid derivative, or non-nucleic acid, and the cleavable linker is cleavable by a cleavage agent.

In a further aspect, the cleavage agent is selected from the group consisting of nuclease enzymes and artificial nucleases.

In another aspect of the invention, a method is provided for amplifying a nucleic acid, comprising: inducing cleavage of a first nucleic acid lock probe of a first ribbon probe as described above using a first nucleic acid sequence, thereby producing a first primer from the first nucleic acid lock probe; combining the first nucleic acid lock probe with a first polymerase and a first circular nucleic acid probe of the first ribbon probe, wherein the first circular nucleic acid probe contains at least one antisense sequence to the first nucleic acid sequence and at least one antisense sequence to a first primer; producing at least one repeat of a sequence copy of a first circular probe by rolling circle amplification using the first polymerase, wherein the sequence copy contains at least the first nucleic acid sequence and repeating, at least once, the inducing, combining, and producing steps using the first nucleic acid sequence contained in the sequence copy.

DETAILED DESCRIPTION OF THE PREFERRED EMBODIMENT

Primer Generation-Rolling Circle Amplification (PG-RCA)

The present invention discloses a method to detect and quantify a nucleic acid sequence of interest using primer generation-rolling circle amplification (PG-RCA). This reaction allows detection of a nucleic acid sequence such as DNA and RNA (e.g., mRNA, rRNA). Furthermore, this reaction is easily applicable to detection of single nucleotide polymorphisms (SNP), biomolecules such as proteins, antigens, peptides, polysaccharides and small molecules, and modified residues resulting from, for example, DNA methylation and posttranslational modification.

Primer generation-rolling circle amplification (PG-RCA) comprises a PG-RCA initiation reaction from a target nucleic acid sequence followed by multiple cycles of primer generation reaction (PGR) and rolling circle reaction (RCR). These reactions are preferably performed under isothermal conditions.

Figure 1:
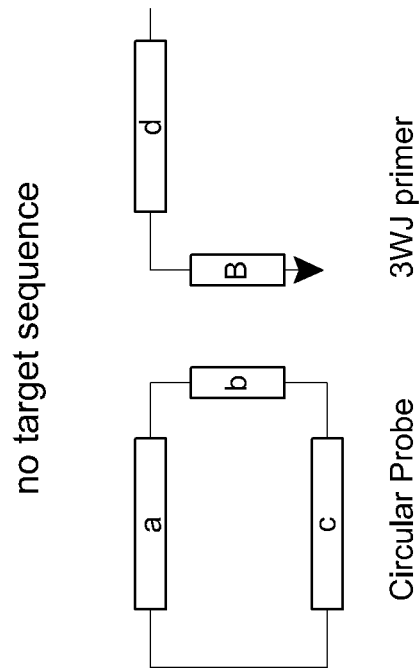
FIG. 1 is a schematic diagram showing the primer generation rolling circle amplification (PG-RCA) initiation reaction.
Figure 1:
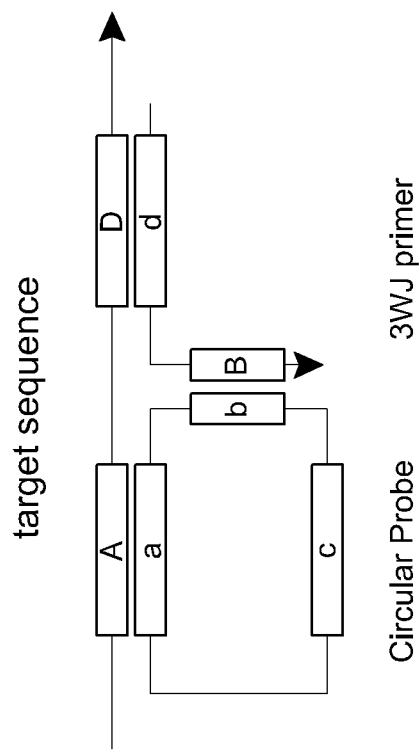

PG-RCA initiation from a target nucleic acid sequence can be done as follows. A 3-way junction (3WJ) primer and circular probe are designed to form a junction with a target nucleic acid sequence only when the target sequence exists in a sample (FIG. 1). In the Figures, oligonucleotides, nucleic acids or polynucleotides are shown as arrows in the 5' end to 3' end direction (the arrow heads are 3' ends). The junction may be a 3-way junction or a more branched structure, e.g. four-way or five-way junction, of nucleic acids. Thus, a DNA polymerase, preferably with strand displacement activity, can start a primer extension reaction from the 3WJ primer on the circular probe, and produce a concatenated sequence of copies of the circular probe by a rolling circle reaction (RCR) under isothermal conditions.

To realize such reaction initiation, the 5' portion of the 3WJ primer is designed to hybridize to the target with a high Tm value similar to the reaction temperature, and its 3' portion is designed to hybridize to a circular probe with a low Tm value, which should be low enough to avoid hybridization between the 3WJ primer and the circular probe when a target sequence doesn't exist. The circular probe is also designed to hybridize to the target with a high Tm value similar to the reaction temperature. Additionally, in order to relieve tension and steric hindrance in a 3WJ complex, at least one unpaired nucleotide can be inserted between the two hybridization sequences of the 3WJ primer, the circular probe or the target.

Furthermore, the circular probe is designed to contain at least one antisense sequence to the primer generation reaction (PGR) initiation sequence, which initiates the following exponential amplification step. Here, PGR is a reaction that is designed to produce at least one nucleic acid primer from a PGR initiation sequence of an RCR product and the resulting primer is designed to prime to a circular nucleic acid probe and initiate RCR. Some examples of PGR are cleavage reaction, strand displacement amplification and RNA transcription as described below in more detail. On the other hand, RCR is designed to produce concatenated sequence copies of the circular probe, in which the resulting product contains at least one PGR initiation sequence in every repeat sequence just like the initial reaction signal.

Figure 2:
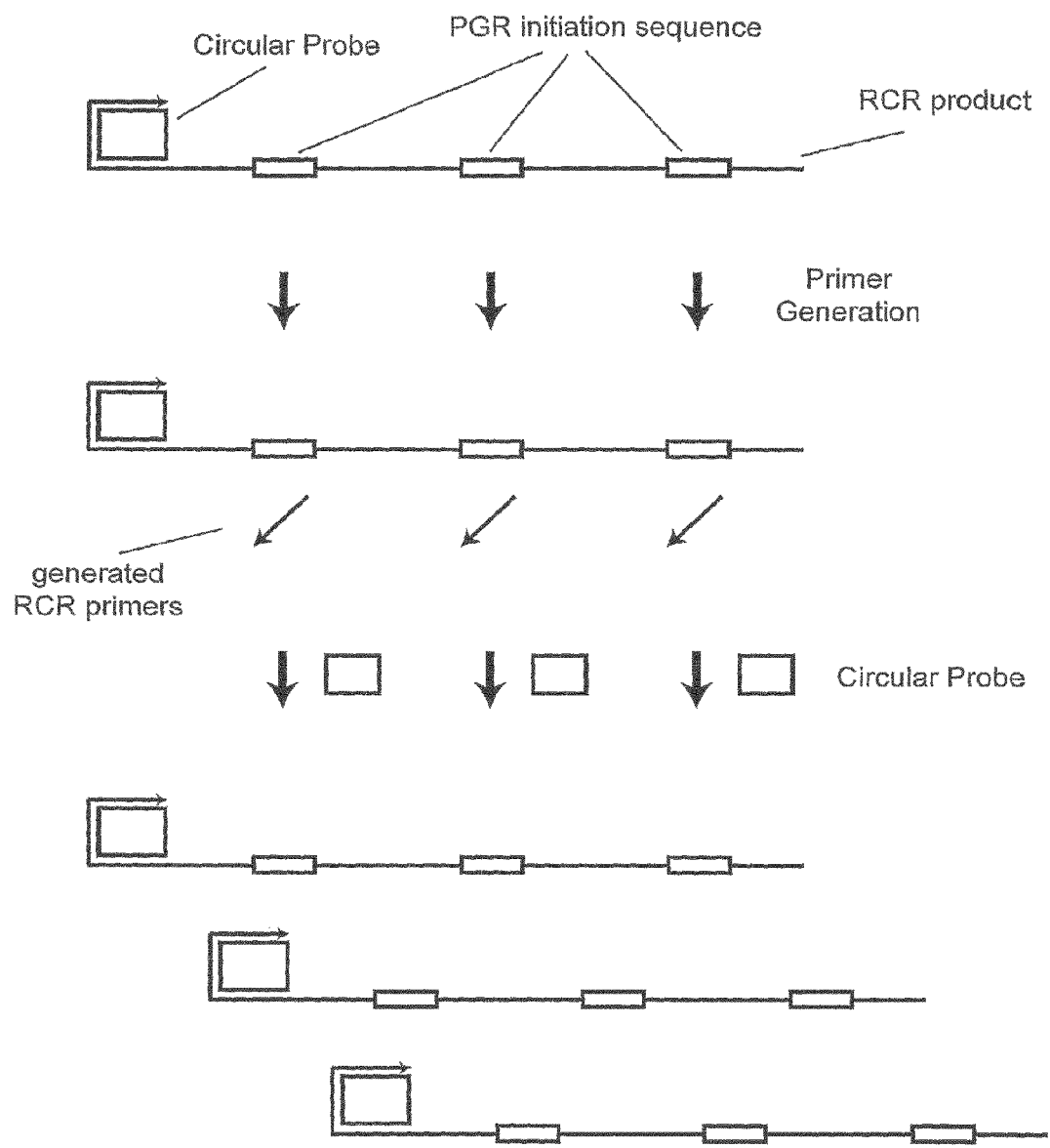
FIG. 2 is a schematic diagram showing the reaction cycles of primer generation reaction (PGR) and rolling circle reaction (RCR).

Therefore, once the first reaction cycle of PGR and RCR starts, the reaction cycle of these reactions continues several times by themselves, because PGR and RCR are designed to initiate each other (FIG. 2). As PGR can produce multiple primers (a number of primers represented by "x") from a PGR initiation sequence and RCR can produce an RCR product containing multiple repeats (a number of repeats represented by "y") of PGR initiation sequences, the amplification factor of the single reaction cycle of PGR and RCR becomes a product of each amplification factor, or a factor of xy. By repeating multiple cycles (a number of cycles represented by "z") of PGR and RCR, the total amplification factor of PG-RCA becomes highly exponential: $(xy)^z$. Therefore, a target nucleic sequence can be detected sensitively and rapidly by the existence of the amplified nucleic acid primers or RCR products and quantified by monitoring the increase of these product amounts in a real-time manner.

Primer Generation Reaction (PGR)

Primer generation reaction (PGR) is an important component of PG-RCA because PGR greatly affects the sensitivity of PG-RCA. As PGR produces more primers from a single PGR initiation sequence or amplification factor, x becomes larger, a cycle of PGR and RCR can produce more RCR primers, RCR products and PGR initiation sequences, and amplification factor xy becomes larger. Also, as PGR produces primers more quickly, more cycles of PGR and RCR can occur so that amplification factor "z" becomes larger. Therefore, it is important to use a PGR that can produce many primers rapidly for maximum sensitivity of PG-RCA. Several examples of primer generation reaction (PGR) are disclosed as follows.

Nuclease-Based Cleavage Reaction

Figure 3A:
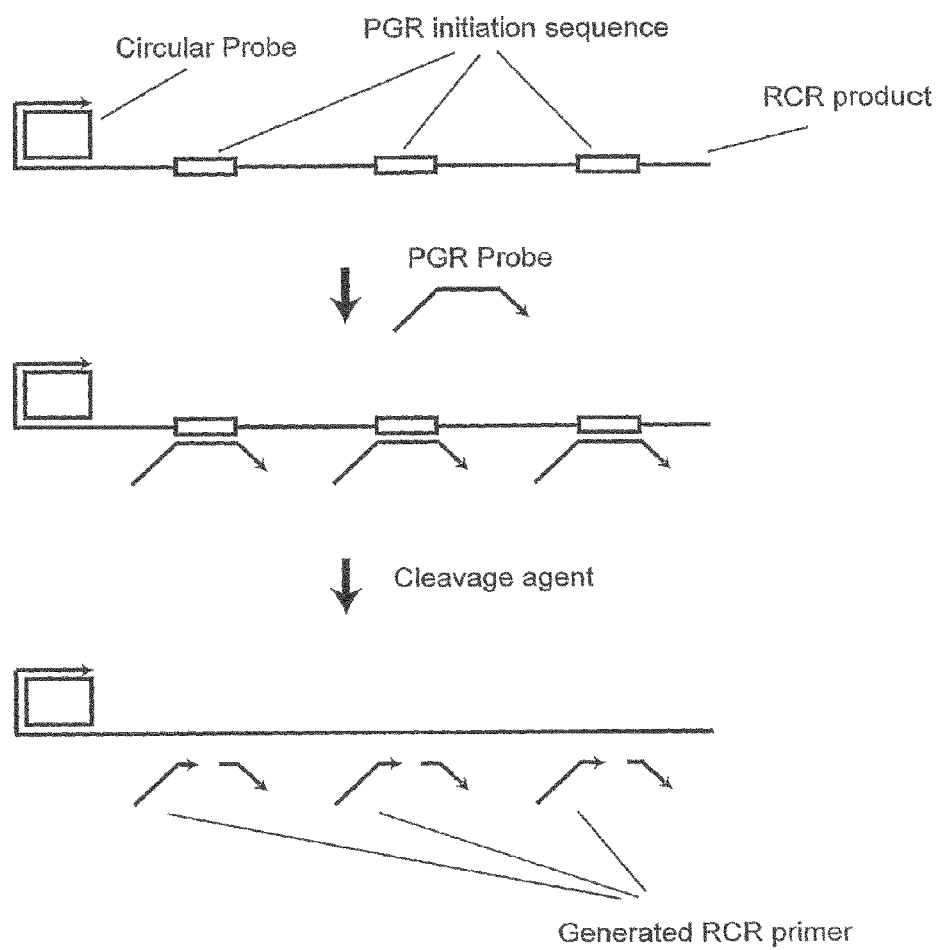
FIGS. 3A and 3B are schematic diagrams showing primer generation reactions employing nuclease-based cleavage reaction.

Nuclease-based cleavage reaction utilizes a nuclease to generate RCR primers. Here, a PGR probe is designed to produce an RCR primer by hybridization to a PGR initiation sequence and following nuclease-based recognition and cleavage (FIG. 3A). In more detail, a PGR probe comprises a 5' end region, which becomes an RCR primer after cleavage, an internal region, which contains a hybridizable sequence to a PGR initiation sequence and a cleavable sequence by a nuclease, and a 3' end region. Preferably nuclease-based cleavage is designed to leave the PGR initiation sequence intact and dissociate cleaved PGR probes from the PGR initiation sequence after cleavage, so that cleavage reaction occurs repeatedly and multiple RCR primers are produced from a single PGR initiation sequence. In one example of nuclease-based cleavage, a nicking endonuclease such as Nb.Bsm I and Nt.BbvC I (available from New England Biolabs (Ipswich, Mass.)) can be utilized, as the enzyme cleaves only one strand in a double strand DNA. Therefore, the enzyme cleaves a PGR probe only when a PGR probe hybridizes to a PGR initiation sequence and leaves a PGR initiation sequence intact. When a circular probe may have the same cleavable sequence as the PGR probe, the sequence of the circular probe can be protected by chemically modified nucleic acids such as methylation modification and phosphorothioate bond modification, so that the nicking enzyme does not cleave the circular probe but the PGR probe. In another example, ribonuclease H (RNaseH), which specifically recognizes and cleaves an RNA strand in an RNA/DNA duplex structure, can be used when a cleavable sequence comprises RNA and a PGR initiation sequence comprises DNA. Preferably, the cleavable sequence comprises at least four bases of RNA, because RNaseH may not recognize and cleave less than four base pairs of RNA/DNA duplex efficiently. In another example, an internal region of a PGR probe is designed to have a high enough Tm or melting temperature to hybridize to a PGR initiation sequence at reaction temperature, and a cleavable sequence is to be in the middle of the internal region, so that each cleaved region has a low enough Tm to dissociate from the PGR initiation sequence spontaneously after cleavage. Furthermore, several endo- or exonucleases such as restriction endonucleases, homing endonucleases, 3'→5' exonucleases and mismatch-specific endonucleases, can generate an RCR primer from a PGR initiation sequence by cleavage reaction.

Several nucleozymes such as deoxyribozyme and ribozyme are known to recognize and cleave specific DNA or RNA. Also, several metal ions such as Ce(IV), Eu(III), Tm(III) and Lu(III) are known to cleave DNA and RNA, and one of skill in the relevant art would know how to control the cleavage site with the help of a nucleic acid probe (see J. Am. Chem. Soc. 126, 1430 (2004)). Therefore, as with nuclease enzymes, it is possible to generate an RCR primer using those artificial nucleases or cleavage agents. In one example, a PGR initiation sequence is designed to be a deoxyribozyme that recognizes and cleaves a PGR probe comprising at least a cleavable RNA sequence by the deoxyribozyme (Proc. Natl. Acad. Sci. USA, 94, 4262 (1997)).

Figure 3B:
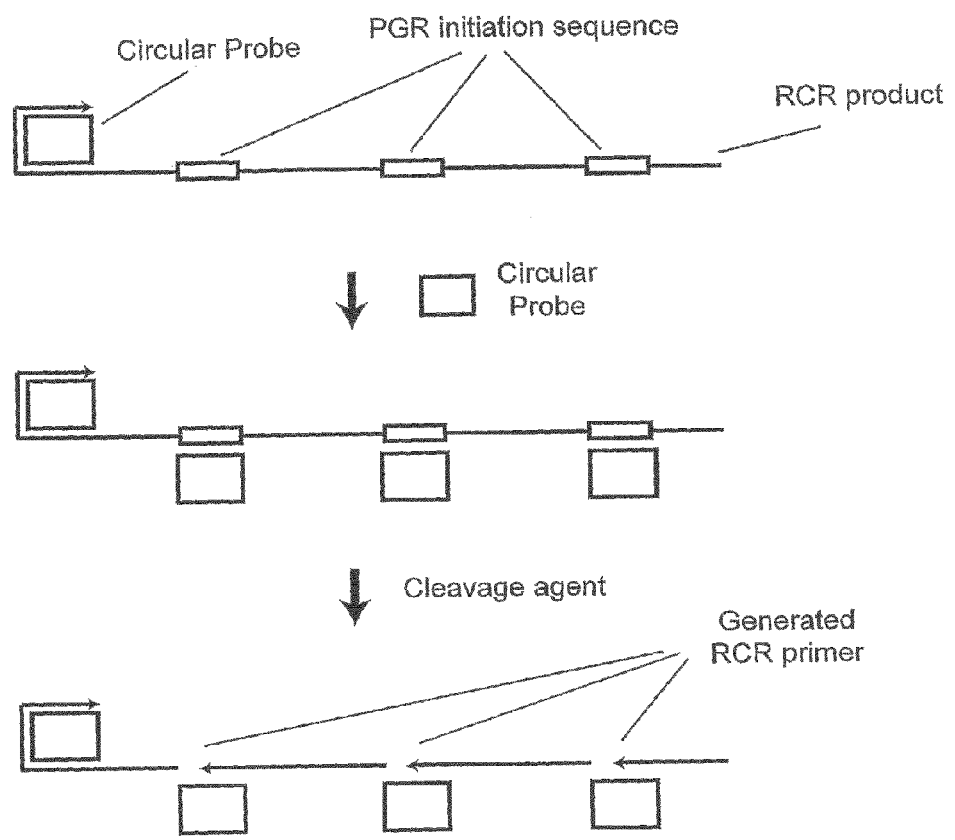

Alternatively, a circular probe is designed to hybridize to a PGR initiation sequence and assist nuclease-based recognition and cleavage of the PGR initiation sequence. In one example, a PGR initiation sequence is designed to contain at least one cleavable sequence by a nicking enzyme. The enzyme can cleave a PGR initiation sequence only when a circular probe hybridizes to the sequence and polymerase can start polymerization from the produced 3' end or primer spontaneously (FIG. 3B). As some nucleozymes leave 2',3'-cyclophosphate or other modification at the cleaved 3' ends (Nucleic Acids Research, 30, 12, e56 (2002)), which may not be an efficient primer, several techniques can be used to generate 3' hydroxyl ends, which are efficient primers. One example is the use of a 3'-phosphatase activity of T4 polynucleotide kinase. Another example is the use of 3'→5' exonuclease activity, which can digest such modified 3' ends and produce 3' hydroxyl ends.

Strand Displacement Amplification

Strand displacement amplification (SDA) can be utilized as a primer generation reaction as shown in FIG. 4.

Figure 4A:
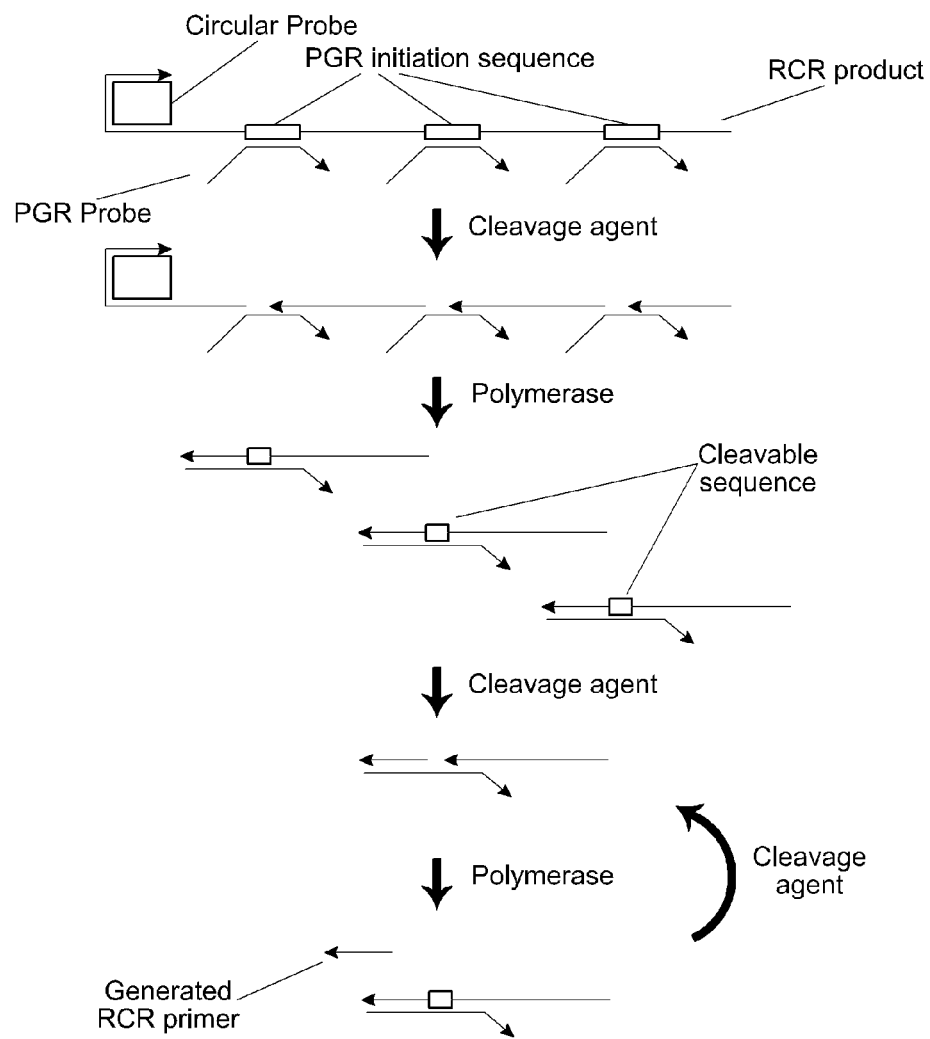
FIGS. 4A and 4B are schematic diagrams showing primer generation reactions employing strand displacement amplification.

In one example of SDA-based PGR, with the help of a PGR probe, a combination of polymerization and nuclease-based cleavage reaction can generate more than one RCR primer from a single PGR initiation sequence (FIG. 4A). In more detail, a PGR probe comprises a 5' end region, which is an antisense sequence to an RCR primer, an internal region, which contains a hybridizable sequence to a PGR initiation sequence and the antisense sequence to a cleavable sequence, and a 3' end region. The 5' region can be either complementary or not complementary to an RCR product as long as synthesized RCR primers can hybridize to another circular probe. Also, preferably, the 3' region is not complementary to an RCR product or not extendable by polymerase using a chemically modified nucleic acid such as 3' phosphate modification, because once a second strand RCR product is synthesized, PGP probes may no longer hybridize to the first strand RCR product or PGR initiation sequences.

Once a PGR probe hybridizes to a PGR initiation sequence of a RCR product, a cleavage agent such as a nicking enzyme cleaves the RCR product and leaves the PGR probe intact. Then, a polymerase with strand displacement activity can extend the cleaved RCR product on the PGR probe to a double strand nucleic acid, which is the starting point for a PGR.

This PGR is a reaction cycle of polymerization and cleavage, which continues repeatedly by itself, preferably under isothermal conditions. As the double strand nucleic acid contains the same cleavage sequence as the RCR product, the cleavage reaction cleaves the newly synthesized strand and leaves the PGR probe intact. Then, a polymerase with strand displacement activity extends the cleaved strand on the PGR probe to a new double strand nucleic acid and displaces the other cleaved strand to a single strand, which becomes an RCR primer. As the double strand nucleic acid is regenerated in the reaction cycle, this PGR continues repeatedly and generates multiple RCR primers.

Figure 4B:
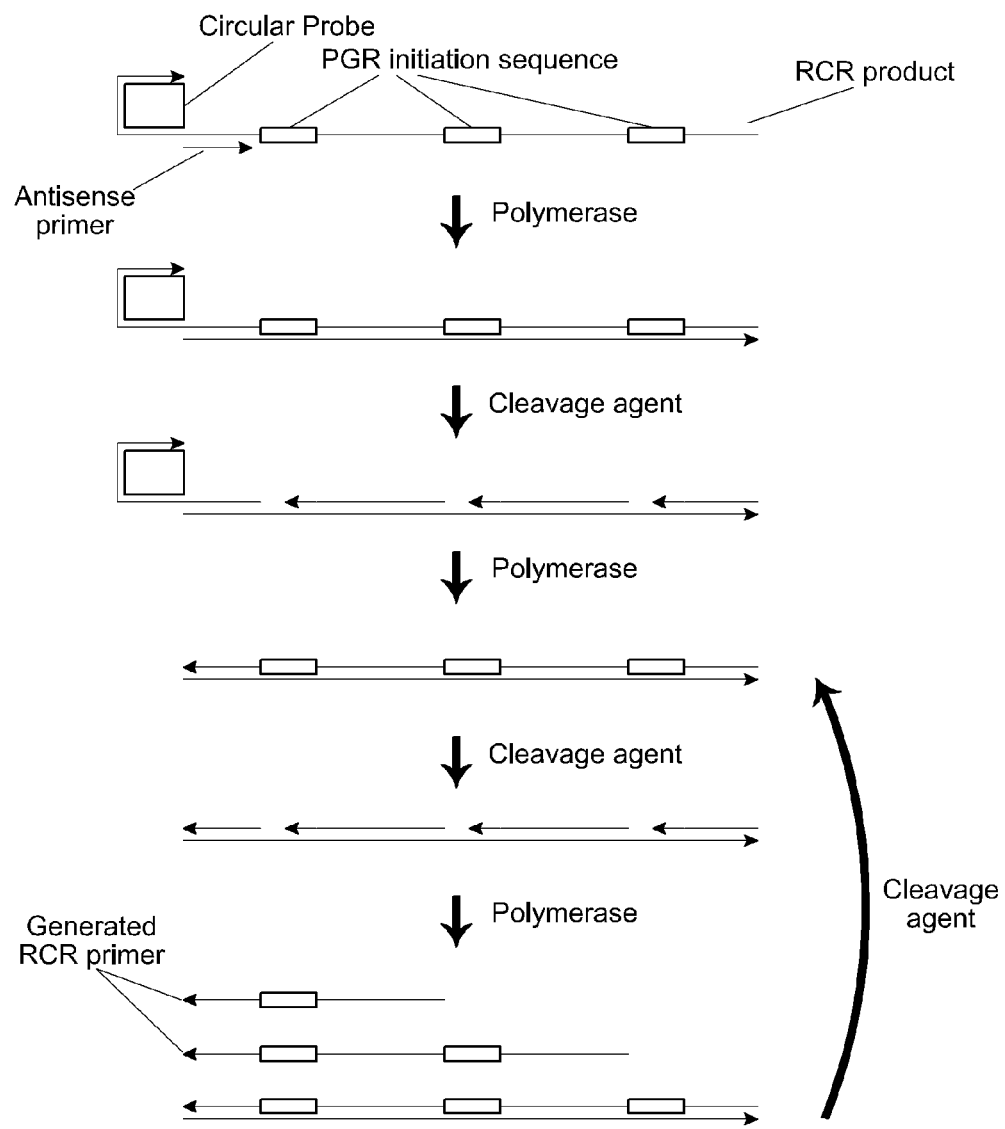

In another example of SDA-based PGR, a combination of polymerization and nuclease-based cleavage reaction can generate more than one RCR primer from a double strand RCR product (FIG. 4B). With the help of an exogenous RCR primer, which can prime to a first strand RCR product, a polymerase synthesizes a double strand RCR product. Then, a cleavage agent such as a nicking enzyme can cleave the first strand RCR product and leave the second RCR product intact. Then, a polymerase with strand displacement activity extends the cleaved first strand RCR product to a double strand nucleic acid, which is a starting point of a PGR.

This PGR is a reaction cycle of polymerization and cleavage, which continues repeatedly by itself, preferably under isothermal conditions. As the double strand nucleic acid contains at least one cleavage sequence, a cleavage agent cleaves the newly synthesized strand and leaves the PGR probe intact. Then, a polymerase with strand displacement activity can extend the cleaved strand on the PGR probe to a new double strand nucleic acid and displace the other cleaved strand to a single strand, which becomes a RCR primer. As the double strand nucleic acid is regenerated in the reaction, this PGR continues repeatedly and generates multiple RCR primers. Furthermore, as the exogenous RCR primer can hybridize to a newly generated RCR primer, another double strand nucleic acid is synthesized by a polymerase, which becomes another starting point for PGR. Furthermore, the exogenous RCR primer can be modified by nucleic acid- or non-nucleic acid-based modification, which polymerase cannot recognize as a template, in order to make the 3' end of the generated RCR primer not complementary to the exogenous RCR primer for higher sensitivity. In one example, such modification is 2'-o-methyl RNA, which cannot be recognized as a template by a variety of polymerases such as Taq and Bst DNA polymerase, or chemical internal linkers such as C3, C9 and C12, which cannot be recognized by polymerase.

Cleavage-Initiated Isothermal Amplification

Figure 5:
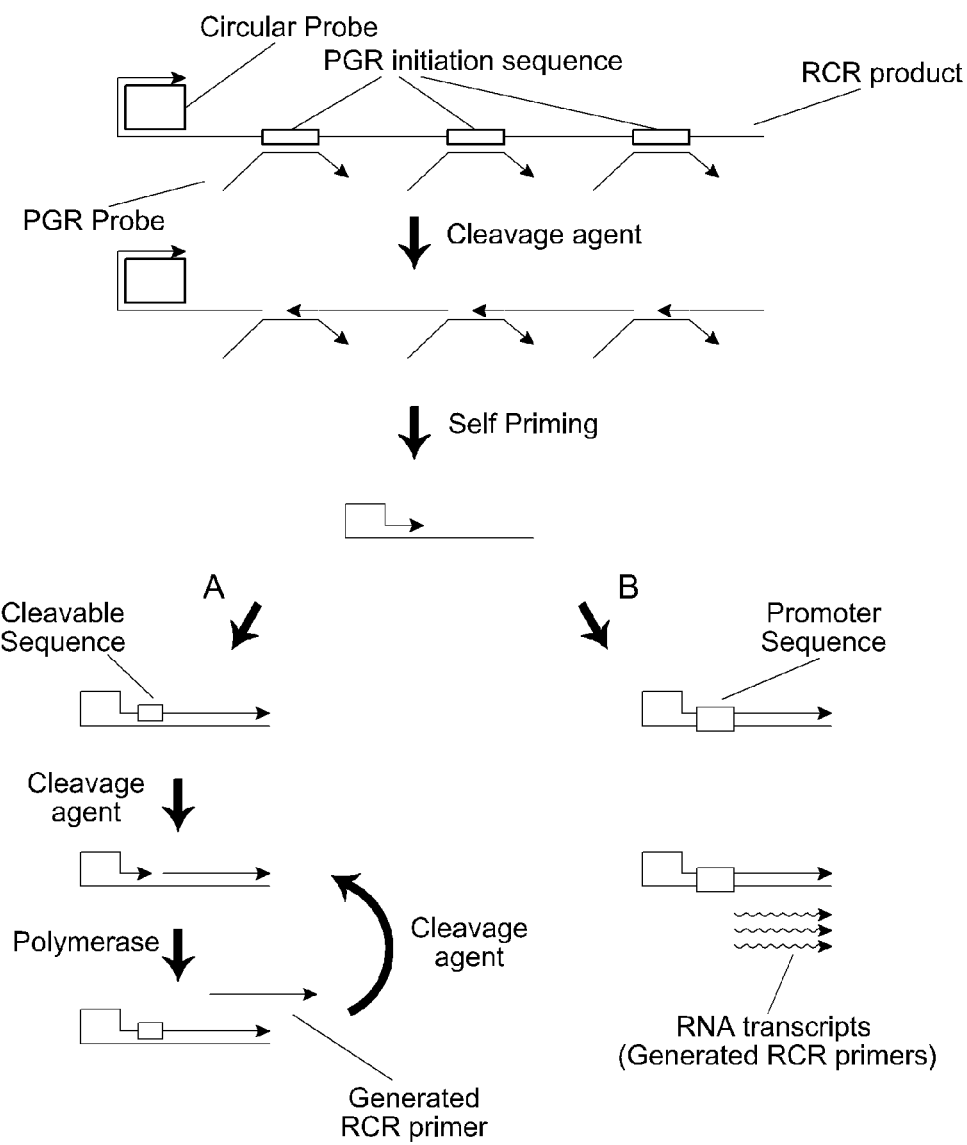
FIG. 5 is a schematic diagram showing a primer generation reaction employing cleavage-initiated isothermal amplification.

The cleavage reaction and the following isothermal amplification can generate multiple primers from a single PGR initiation sequence (FIG. 5). A linear nucleic acid probe can be generated from a linear or circular PGR probe upon nuclease-based cleavage induced by a PGR initiation sequence (FIG. 5). The resulting linear probe is designed to be self-primed and a polymerase extends the 3' end to form a hairpin nucleic acid, which becomes a starting point for PGR. In one example, the hairpin nucleic acid is designed to have a cleavable region by a nuclease or non-nuclease agent (shown by path A in FIG. 5). A polymerase with strand displacement activity and cleaving agent continuously generate single strand nucleic acids, which work as RCR primers, by strand displacement amplification (SDA). In another example, the hairpin nucleic acid is designed to contain a promoter sequence that can initiate RNA transcription (shown by path B in FIG. 5). RNA polymerase continuously synthesizes RNA transcripts, which work as RCR primers. In another example, the hairpin structure of the hairpin nucleic acid is designed as a bubble structure that can initiate RNA transcription by RNA polymerase. RNA polymerase continuously synthesizes RNA transcripts, which work as RCR primers.

3-Way Junction Isothermal Amplification

Figure 6:
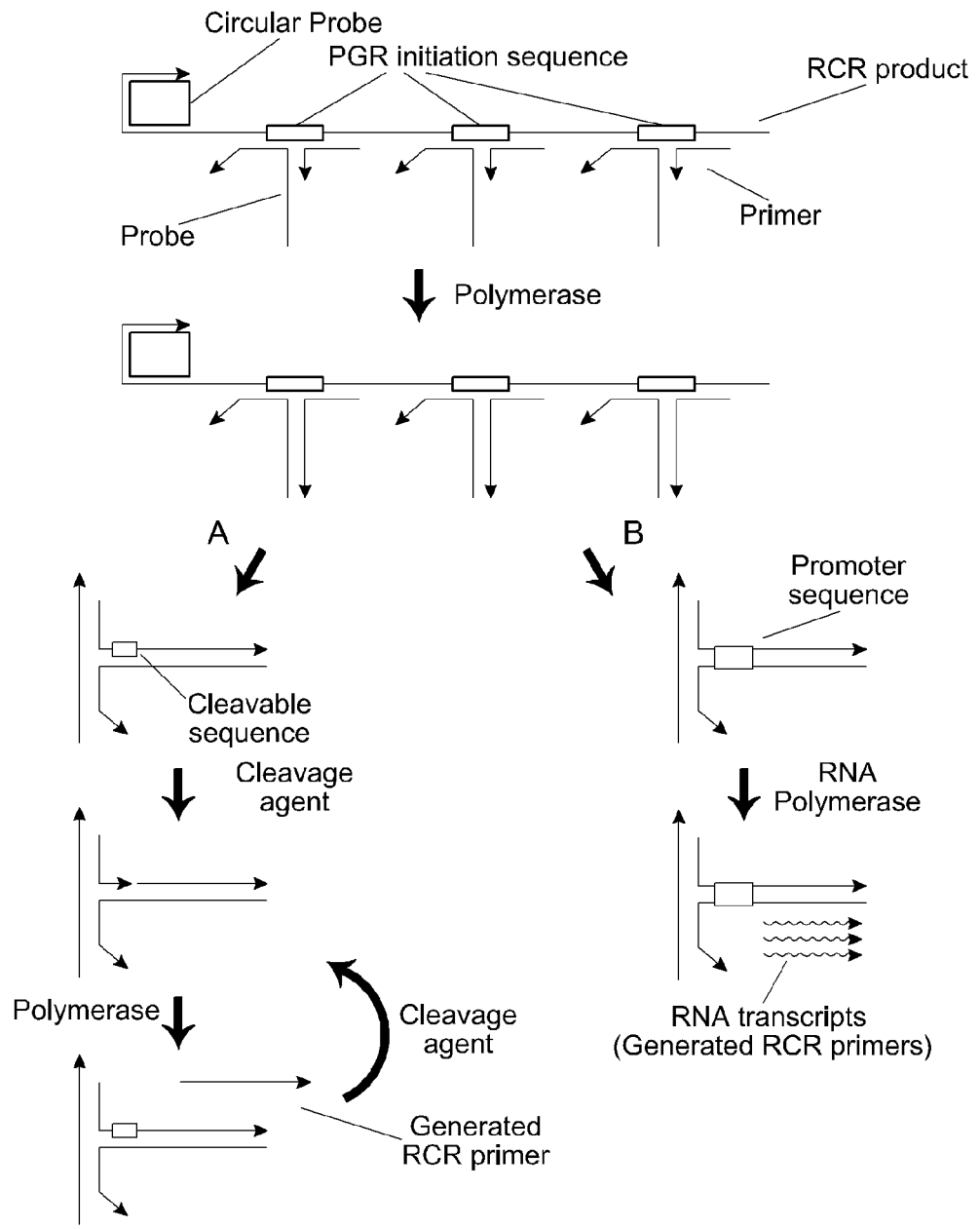
FIG. 6 is a schematic diagram showing a primer generation reaction employing three-way junction isothermal amplification.

It is possible to generate multiple primers from a single PGR initiation sequence by forming a 3-way junction or more branched structure, e.g. four-way or five-way junction, of nucleic acids, followed by isothermal amplification (FIG. 6). A nucleic acid primer and probe are designed to form a stable 3WJ or higher branched structure with a PGR initiation sequence. The 3' end portion of the primer is complementary to the circular probe, but short enough to prevent hybridization to the circular probe by itself. Therefore, only with the assistance of a PGR initiation sequence, polymerase can extend the primer on the probe to a double strand nucleic acid, which is a starting point for PGR.

In one example, the double strand nucleic acid is designed to have a cleavable region by a nuclease or non-nuclease agent (shown by path A in FIG. 6). A polymerase, preferably with strand displacement activity, and cleaving agent continuously generate single strand nucleic acids, which become RCR primers, by strand displacement amplification (SDA). In another example, the double strand nucleic acid is designed to contain a promoter sequence that can initiate RNA transcription (shown by path B in FIG. 6). RNA polymerase continuously synthesizes RNA transcripts, which become RCR primers.

3-Way Junction RCR

Figure 7:
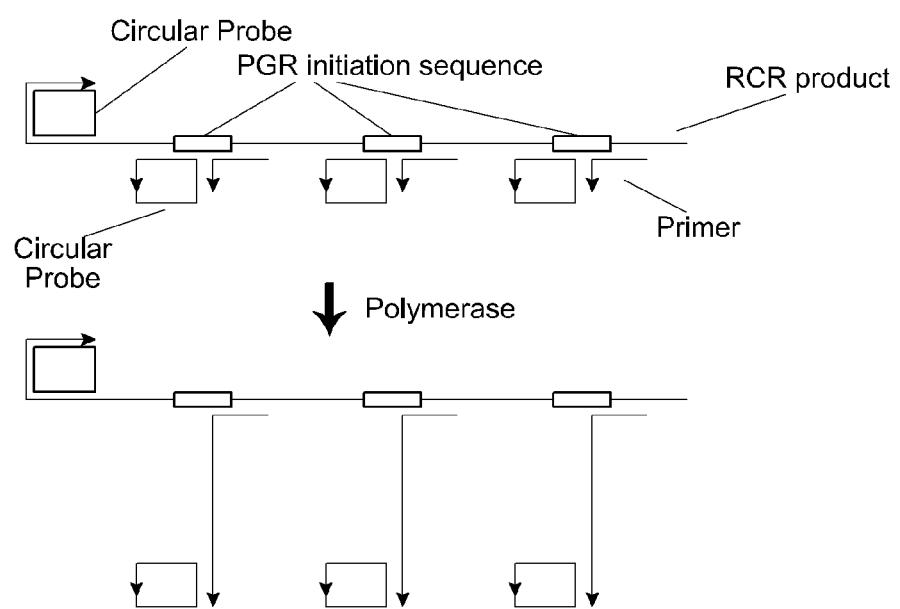
FIG. 7 is a schematic diagram showing a primer generation reaction employing a three-way junction rolling circle reaction.

PGR is not necessarily a reaction to synthesize new 3' ends of a nucleic acid. It is possible to generate multiple primers from a PGR initiation sequence by utilizing a three-way junction (3WJ) or more branched structure, e.g. four-way or five-way junction, of nucleic acids. A nucleic acid primer and circular nucleic acid probe are designed to form a stable 3WJ or higher branched structure with a PGR initiation sequence (FIG. 7). The 3' end portion of the primer is complementary to the circular probe, but short enough to prevent hybridization to the circular probe by itself. Therefore, the primer becomes a RCR primer only with the assistance of a PGR initiation sequence though the primer is not changed in terms of its chemical structure.

PG-RCA Initiation Reaction for Detection of Other Molecules

In order to detect a target molecule, as long as the molecule can induce and initiate PGR or RCR, reaction cycles of PGR and RCR make it possible to detect the molecule very sensitively and rapidly, therefore PG-RCA is a very versatile technology for in vitro diagnostics.

Detection of Nucleic Acid Sequence

For detection of a nucleic acid sequence of interest, the above mentioned PGR reactions such as nuclease-based cleavage reaction, cleavage-initiated isothermal amplification and 3WJ-isothermal amplification can be utilized by designing PGR to initiate from the nucleic acid sequence instead of a PGR initiation sequence. In one example, PG-RCA can be initiated by nuclease-based cleavage reaction. When a target DNA sequence has a sequence cleavable by a nicking enzyme and a circular probe is designed to hybridize to the sequence, the enzyme cleaves the target sequence only when the circular probe hybridizes to the sequence and polymerase can extend the produced 3' end or primer on the circular probe and PG-RCA starts. Furthermore, as a variety of restriction enzymes such as HhaI, AluI, TaqI and HaeII are known to cleave DNA and RNA strands in a DNA/RNA duplex structure (Nucleic Acid Res., 1980, 13, 2939), a nuclease-based cleavage reaction can be utilized without reverse transcription. Furthermore, as reverse transcription converts RNA into single- or double-strand cDNA, the PG-RCA initiation reaction can be designed to start from the converted cDNA. Furthermore, several conventional techniques such as RNA protection assay can be utilized as PG-RCA initiation reaction using a circular probe or PGR probe instead of a protection probe from nuclease.

Detection of SNPs

Several techniques have been established to detect single nucleotide polymorphisms (SNP), and some of these can be utilized as a PG-RCA initiation reaction to detect SNP. In one example, the above explained nuclease-based cleavage reaction or cleavage-initiated amplification can be designed to detect SNPs using a mismatch-sensitive nuclease such as Surveyor nuclease (available from Transgenomic, Inc. (Omaha, Nebr.)), Cleavase (available from Third Wave Molecular Diagnostics (Madison, Wis.)), or RNaseH (Analytical Biochem., 333, 246 (2004)).

Detection of DNA methylation

A variety of nucleases, such as HaeII, NotI and SmaI, are sensitive to methylation modification of DNA and do not cleave such modified sequences. Thus it is possible to distinguish methylated and unmethylated DNA by PG-RCA using the above explained nuclease-based cleavage reaction or cleavage-initiated amplification using a methylation-sensitive nuclease. Therefore, DNA methylation modification can be detected very sensitively by PG-RCA.

Detection of Biological Molecules

PG-RCA can be used to detect a biological molecule of interest such as a protein, antigen, peptide, polysaccharide, or small molecule, and a modified residue on a biological molecule such as methylation on DNA and phosphorylation on protein using a nucleic-acid labeled recognition agent.

In one example, PG-RCA can detect a nucleic acid label attached to a recognition agent such as an antibody, antigen, protein, peptide, aptamer or polymer, which specifically binds to a molecule of interest. By incubating a molecule of interest with a labeled agent and washing an unbound agent, it is possible to detect a molecule of interest by detecting the nucleic acid label attached to the molecule. The nucleic acid label can be a nucleic acid sequence or a molecule that can initiate PGR or RCR. Therefore, a molecule of interest can be detected and quantified by the amount of PG-RCA product. Some examples of such a nucleic acid are a nucleic acid primer that is complementary to a circular probe and a double strand nucleic acid or hairpin-shape double strand nucleic acid that can generate RCR primers by SDA or RNA amplification.

In another example, a proximity assay, in which a set of recognition agents can form a complex only when a molecule of interest exists, can initiate PG-RCA to detect a molecule of interest. One of skill in the relevant art would understand how to perform such a proximity assay, as evidenced by Nat. Biotech., 14, 1714 (1996), Nat. Biotech. 20, 473 (2002), and Nucleic Acids Research, 33, 6, e64, (2005). Some examples of a recognition agent are antibody, antigen, protein, peptide, aptamer and polymer, labeled with a nucleic acid sequence or a molecule that can initiate PG-RCA. In one example, one agent is labeled with a primer and the other with a circular probe, so that a RCR starts only when two agents are in close proximity. In another example, one agent is labeled by a short nucleic acid primer, which is complementary to a circular probe but too short to hybridize to a circular probe, and the other is labeled by a nucleic acid probe, which is complementary to the circular probe and long enough to hybridize to the circular probe stably. Thus, a circular probe can hybridize to the short primer only when both agents are in close proximity with the help of a molecule of interest and initiate PG-RCA. Therefore, a molecule of interest can be detected and quantified by the amount of PG-RCA product.

Ribbon Probe for PG-RCA

Figure 8A:
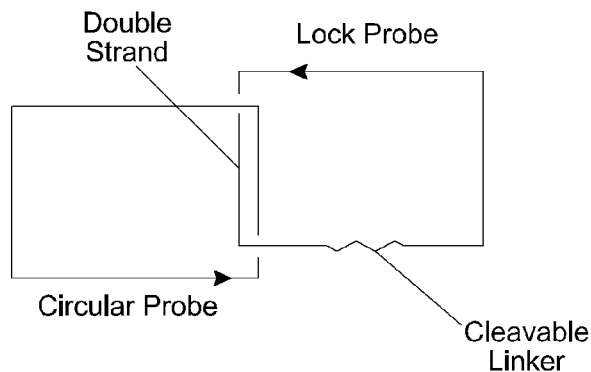
FIGS. 8A-8C are schematic diagrams showing ribbon probes.
Figure 8B:
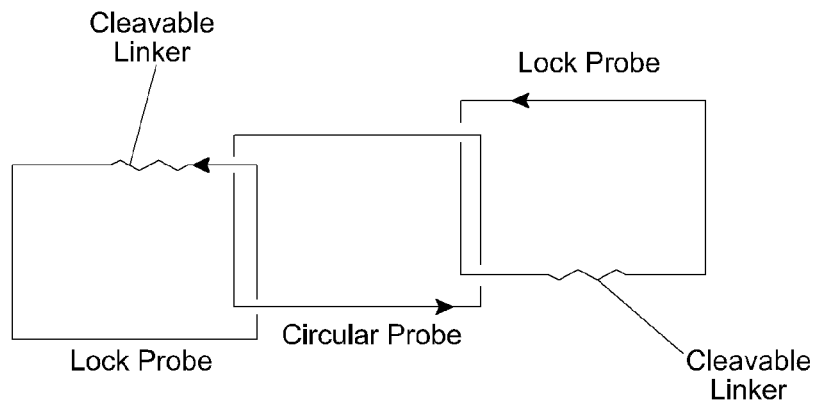
Figure 8C:
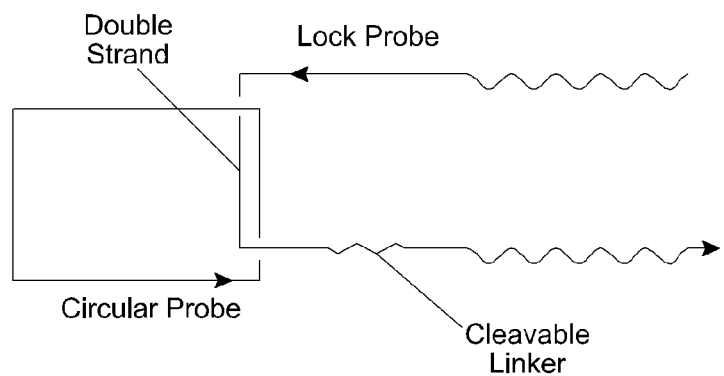

A ribbon probe is a circular nucleic acid probe hybridized by at least one nucleic acid lock probe that contains at least one cleavable linker. The circular probe and lock probe are unable to dissociate from each other without cleaving the cleavable linker. A lock probe is a circular nucleic acid (FIG. 8A, 8B), or a linear nucleic acid long enough not to dissociate from the circular probe by itself (FIG. 8C). A cleavable linker comprises DNA, RNA, modified nucleic acid or cleavable molecule. Because a circular probe padlocked by a circular or long linear template is not an efficient template for rolling circle amplification (Nucleic Acid Research, 26, 22, 5073 (1998)), a ribbon probe can minimize false positive PG-RCA amplification due to non-specific priming of a nucleic acid in a sample to a circular probe. Furthermore, the circular probe contains at least one antisense sequence to a PGR initiation sequence for PG-RCA.

Figure 9:
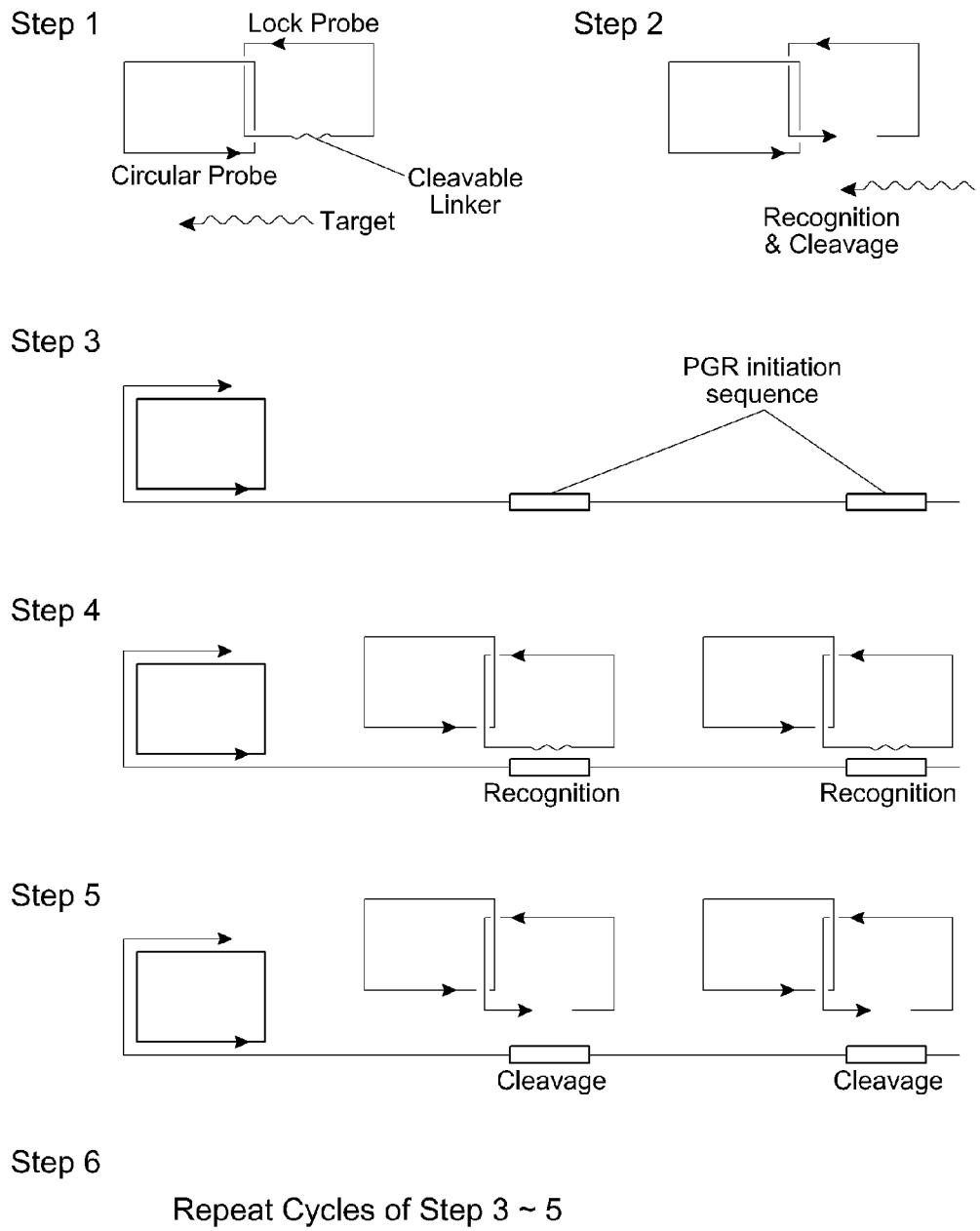
FIG. 9 is a schematic diagram showing PG-RCA using a ribbon probe.

PG-RCA using a ribbon probe can be done by a nuclease-based cleavage reaction. Once the lock probe is cleaved by a cleaving agent, a RCR primer, which is generated from the lock probe, hybridizes to the circular probe and initiates RCR (FIG. 9). The circular probe is designed to produce a RCR product containing more than one PGR initiation sequence, which induces cleavage of a cleavable linker of another ribbon probe.

For more efficient cleavage, the region that becomes a 3' end after cleavage is designed to be complementary to a circular probe but remain single stranded by the physical property of a nucleic acid. A nucleic acid is more rigid in a double strand form than in a single strand form, and double strand DNA requires at least 126 base pairs to form a complete circle (Gene, 211, 277 (1998), J. Am. Chem. Soc, 118, 1587 (1996) and Proc. Natl. Acad. Sci. USA, 78, 4833 (1981)). Therefore, the length of a double strand that a single strand circular probe smaller than 126 bases can form with another nucleic acid is limited. Alternatively, a spacer region, which is a nucleic acid sequence or non-nucleic acid linker that does not hybridize to a circular probe, can be incorporated between a region that becomes an RCR primer after cleavage and a region that associates with a circular probe. Alternatively, an RCR primer can be generated from a lock probe by cleavage and digestion of the cleaved 3' ends. In one example, a 3'→5' exonuclease, or the exonuclease activity of a polymerase, can be utilized to digest the 3' ends after cleavage of the cleavable linker. Alternatively, a target molecule may be cleaved together with a cleavable linker.

EXAMPLES

In the following examples, nucleic acid sequences are described from 5' end (left) to 3' end (right) direction. DNA is shown in small letters, RNA is in large capitals and 2'-o-methyl-RNA is in italicized large capitals. 5'-end and 3'-end phosphate modifications are described as /5phos/ and /3phos/, respectively. Nt.BbvC I and Nb.Bsm I recognition sequences are underlined and double-underlined, respectively. An internal C3 linker is shown as /isp3/.

Example 1

Synthesis of a Circular Probe

A linear nucleic acid probe (SEQ ID NO:1) was purchased from Integrated DNA Technologies (Coralville, Iowa). A circular probe was synthesized from this linear probe using Circligase from Epicentre (Madison, Wis.) following the manufacturer's protocol. After circularization, uncircularized probes were removed by exonuclease I (Epicentre, Madison, Wis.)) and exonuclease III (New England Biolabs, Ipswich, Mass.) treatment at 37° C. overnight following G25 spin column punctuation (Amersham Biosciences, Piscataway, N.J.). Alternatively, a circular probe was purified by 7M Urea-5% polyacrylamide gel electrophoresis and following exonuclease I and III treatment.

```
                                                  SEQ ID NO:1
/5phos/tgcgacgaccgttgcgggcagtgatctccttctgcatcctg
tcgagtgatgtattcggtgtcccagccgcagtgaa
```

Example 2

RCR Reaction from 3-Way Junction Structure

A circularizable probe (SEQ ID NO:2), 3WJ primer (SEQ ID NO:3) and target DNA (SEQ ID NO:4) were obtained from Integrated DNA Technologies. Bst DNA polymerase large fragment was purchased from New England Biolabs. A circular probe was synthesized as shown in Example 1 except using a circularizable probe with a different sequence.

3WJ-RCA was performed using 4 µM circular probe and 500 nM 3WJ primer as a 3WJ primer with or without 500 nM target DNA. The 3WJ primer was designed to form two unpaired thymidines in a 3WJ structure comprising the C-probe, the 3WJ primer and the target. The reaction was performed in a 10 III buffer comprising 400 µM dNTP (Promega), 1× Themopol reaction buffer (New England Biolabs), and 0.08 U/µl Vent (exo-) DNA polymerase (New England Biolabs), at 69° C. for 65 hours after 3-min denaturation at 94° C.

The reaction products were analyzed by PCR and a subsequent 1.5% agarose gel analysis. Concatenated product was observed only with the 500 mM target molecule. The PCR conditions were: 10 µl reaction comprising 400 µM dNTP (Promega), 1× Themopol reaction buffer (New England Biolabs), 0.04 U/µl Vent (exo-) DNA polymerase (New England Biolabs), 1/125000 diluted SybrGreen1 (Molecular Probes), 10 nM 6-carboxyfluorescein (Molecular Probes), 0.5 µM sense and antisense PCR primers (SEQ ID NO:5, 6) and 1 µl of the above reaction product. Temperature cycle: 3-minute initial denaturation at 95° C. and 34 cycles of 95° C. for 15 seconds and 69° C. for 5 minutes.

```
                                                  SEQ ID NO:2
/5Phos/tttctgacggcaacttcaactggggccgggttgtcgccctttt
tctactttgccagcaaactggtgctcaa ggccctgtg SEQ ID NO:3
ggcatacccctcgtagatgggttagtttg SEQ ID NO:4
cacagggccttgagcaccccatctacgaggggtatgcc SEQ ID NO:5
ggcatacccctcgtagatggg SEQ ID NO:6
tttctgacggcaacttcaactg
```

Example 3

PG-RCA Using Nuclease-Based Cleavage Reaction

A PGR Probe (SEQ ID NO:7), circularizable probe (SEQ ID NO:8) and nucleic acid sequence of interest (SEQ ID NO:9) were obtained from Integrated DNA Technologies. Bst DNA polymerase large fragment was purchased from New England Biolabs and Thermo stable RNaseH was from Epicentre. A circular probe was synthesized as shown in Example 1 except using a circularizable probe with a different sequence.

PG-RCA was performed at 65° C. for 1 hour in a 10 µl reaction with the following components: 400 µM dNTP, 500 nM PGR probe, 10 µM circular probe, 1× Thermopoly Buffer (New England Biolabs), 1/125000 diluted SybrGreen I (Invitrogen, Carlsbad, Calif.), 0.3 U Thermostable RNaseH and 0.8 U Bst DNA polymerase large fragment. The reaction was monitored in a real-time manner by increase of fluorescent intensities on iCycler (Biorad Laboratories, Hercules, Calif.) and analyzed on agarose gel with SybrGold (Invitrogen) staining. An increase in fluorescent signal intensities was observed depending on the amount of the nucleic acid sequence of interest ($3 \times 10^{10}$, $3 \times 10^9$, $3 \times 10^8$, $3 \times 10^7$, $3 \times 10^6$, $3 \times 10^5$, $3 \times 10^4$ or 0 molecules in 10 µl).

```
                                                  SEQ ID NO:7
agaggactattacccgaggagtCUGAcggcaacttcaactggUUU SEQ ID NO:8
/5phos/agtcctctctgacggcaacttcaactggag
actcctcgggtaat SEQ ID NO:9
ccagttgaagttgccgtcagaUUU
```

Example 4

Three-Way Junction RCR-Initiated PG-RCA Using Strand Displacement Amplification A circularizable probe (SEQ ID NO:10), 3WJ primer (SEQ ID NO:11), antisense primer (SEQ ID NO:12) and a nucleic acid sequence of interest (SEQ ID NO:13) were purchased from Integrated DNA Technologies. A circular probe was synthesized as shown in Example 1 except using a circularizable probe with a different sequence.

PG-RCA was conducted at 64° C. for 1 hour in a 10 µl reaction comprising 400 µM dNTP, 500 nM 3WJ primer, 500 nM antisense primer, 1 µM circular probe, 4 mM $MgSO_4$, 50 mM KCl, 1× Themopol reaction buffer (New England Biolabs), 1/125000 diluted SybrGreenI (Invitrogen), 0.8 U Bst DNA polymerase large fragment (New England Biolabs) and 1 U Nb.Bsm I (New England Biolabs). The reaction was monitored in a real-time manner by increase of fluorescent intensities on iCycler (Biorad Laboratories) and analyzed on agarose gel with SybrGold (Invitrogen) staining. An increase in fluorescent signal intensities was observed depending on the amount of the nucleic acid sequence of interest ($3 \times 10^8$, $3 \times 10^6$, $3 \times 10^4$, $3 \times 10^2$, $3 \times 10^0$, $3 \times 10^{-2}$ or 0 molecules in 10 µl).

```
                                                 SEQ ID NO:10
/5phos/tgcgacgaccgttgcgggcagtgatctccttctgcatcctgt
cgagtgatgtattcggtgtcccagcc gcagtgaa SEQ ID NO:11
aggagctagtatcttgatcttcattgtgctgggtggcggtcg SEQ ID NO:12
agtgatgtattcggtgtcccagccgcagt SEQ ID NO:13
cgacaggatgcagaaggagatcactgcccgcccacccagcacaat
gaagatcaagatactagctcctaaaaa
```

Example 5

Synthesis of a Ribbon Probe

A circularizable probe (SEQ ID NO:14) and circularizable lock probe (SEQ ID NO: 15) were purchased from Integrated DNA Technologies. A circular lock probe was synthesized from a circularizable look probe by Cirdligase (Epicentre) following the manufacturer's protocol, and uncircularized look probes were removed by exonuclease T (New England Biolabs) and exonuclease I (Epicentre) and subsequent G25 spin column (Amersham Biosciences) purification. Using the circular lock probe as a template, a circularizable probe was circularized by T4 DNA ligase (Epicentre) and uncircularzed probes were removed by exonuclease T and I and following G25 spin column purification. The resulting probe is a ribbon-shape probe composed of circular probe and circular lock probe padlocked with each other.

```
                                            SEQ ID NO:14
/5phos/agtcctctctgacggcaacttcaactgg
agactcctcgggtaat
```

```
                                            SEQ ID NO:15
/5phos/tattacccgaggagtCUGAcggcaactt
caactggagaggac
```

Example 6

PG-RCA Using a Ribbon Probe

A nucleic acid of interest (SEQ ID NO: 16) was purchased from Integrated DNA Technologies. A ribbon probe was synthesized as shown in Example 5.

PG-RCA was performed at 60° C. for 1 hour in 101 reaction with the following components: 400 μM dNTP, 80 nM ribbon probe, 1× Thermopoly Buffer (New England Biolabs), 1/125000 diluted SybrGreen I (Invitrogen), 0.3 U Thermostable RNaseH and 0.8 U Bst DNA polymerase large fragment. The reaction was monitored in a real-time manner by the increase in fluorescent intensities on iCycler (Biorad Laboratories) and analyzed on agarose gel with SybrGold (Invitrogen) staining.

An increase in fluorescent signal intensities was observed depending on the amount of the target molecule ($3 \times 10^{10}$, $3 \times 10^9$, $3 \times 10^8$, $3 \times 10^7$, $3 \times 10^6$, $3 \times 10^5$, $3 \times 10^4$ or 0 molecules in 10 μl).

```
ccagttgaagttgccgtcagaUUU       SEQ ID NO: 16
```

---

What is claimed is:

1. A method of amplifying a nucleic acid, comprising:
    (a) providing a first linear nucleic acid primer;
    (b) combining said first linear nucleic acid primer with a polymerase and a circular nucleic acid probe, wherein said circular nucleic acid probe contains at least one antisense sequence to a second nucleic acid sequence and at least one antisense sequence to said first linear nucleic acid primer;
    (c) producing at least one repeat of an antisense copy of said circular nucleic acid probe by rolling circle amplification using said polymerase, wherein said antisense copy contains at least said second nucleic acid sequence;
    (d) generating a plurality of second linear nucleic acid primers from each copy of said second nucleic acid sequence in each antisense copy by hybridizing a nucleic acid molecule to said second nucleic acid sequence in each antisense copy, by
        (i) cleaving said antisense copy and/or said nucleic acid molecule by a cleavage agent, thereby generating precursors of said second linear nucleic acid primers capable of self-priming;
        (ii) self-priming said precursors of said second linear nucleic acid primers; and
        (iii) extending the self-primed precursors by
            (1) polymerase followed by cleavage with said cleavage agent, or
            (2) RNA polymerization, thereby generating said plurality of second linear nucleic acid primers;
    (e) hybridizing said second linear nucleic acid primers to a plurality of said circular nucleic acid probes; and
    (f) repeating steps (c), (d) and (e) at least once.

2. The method of claim 1, wherein at least a portion of said first linear nucleic acid primer hybridizes to a molecule to be detected, and further comprising:
    (g) detecting a product of said polymerase or said second linear nucleic acid primer as an indication of the presence of said molecule.

3. The method of claim 1, wherein said nucleic acid molecule hybridizes to at least a portion of said second nucleic acid sequence.

4. The method of claim 3, wherein at least a portion of said nucleic acid molecule does not hybridize to said second nucleic acid sequence.

5. The method of claim 3, wherein said nucleic acid molecule is a linear nucleic acid molecule.

6. The method of claim 3, wherein said nucleic acid molecule is a circular nucleic acid molecule.

7. The method of claim 3, wherein a second nucleic acid molecule hybridizes to at least a portion of said second nucleic acid sequence.

8. The method of claim 7, wherein said second linear nucleic acid primers are generated by extension and cleavage of said precursors of second nucleic acid molecule.

9. The method of claim 7, wherein said second linear nucleic acid primers are generated by RNA polymerization.

10. The method of claim 1, wherein, after said cleavage of said antisense copy, said second linear nucleic acid primers are generated by repeated extension and cleavage of said antisense copy.

11. The method of claim 1, wherein said additional second linear nucleic acid primers are generated by extension and cleavage of said precursors of said second linear nucleic acid primers.

12. The method of claim 1, wherein step (a) comprises hybridizing or binding at least a portion of a nucleic acid label to a molecule to be detected, thereby generating at least said first linear nucleic acid primer, and further comprising:
    (g) detecting a product of said polymerase or said second linear nucleic acid primer as an indication of the presence of said molecule to be detected.

13. The method of claim 12, wherein said molecule to be detected is selected from the group consisting of DNA, RNA, proteins, antigens, peptides, polysaccharides, small molecules, methylated DNA, post-translationally modified nucleic acids, and single nucleotide polymorphisms.

14. A method for amplifying a nucleic acid, comprising:
    providing a first ribbon probe, comprising a circular nucleic acid probe and a nucleic acid lock probe, wherein said nucleic acid lock probe contains at least a cleavable linker, and said circular nucleic acid probe and said lock probe are unable to dissociate without cleaving said cleavable linker;

inducing cleavage of a first nucleic acid lock probe of said first ribbon probe using a first nucleic acid sequence, thereby producing a first primer from said first nucleic acid lock probe;

combining said first nucleic acid lock probe with a first polymerase and a first circular nucleic acid probe of said first ribbon probe, wherein said first circular nucleic acid probe contains at least one antisense sequence to said first nucleic acid sequence and at least one antisense sequence to a first primer;

producing at least one repeat of an antisense copy of a first circular probe by rolling circle amplification using said first polymerase, wherein said antisense copy contains at least said first nucleic acid sequence and repeating, at least once, said inducing, combining, and producing steps using said first nucleic acid sequence contained in said antisense copy.

\* \* \* \* \*

SEQUENCE LISTING

```
<160> NUMBER OF SEQ ID NOS: 16

<210> SEQ ID NO 1
<211> LENGTH: 76
<212> TYPE: DNA
<213> ORGANISM: Artificial Sequence
<220> FEATURE:
<223> OTHER INFORMATION: Synthetically prepared oligonucleotide sequence

<400> SEQUENCE: 1
tgcgacgacc gttgcgggca gtgatctcct tctgcatcct gtcgagtgat gtattcggtg       60
tcccagccgc agtgaa                                                      76

<210> SEQ ID NO 2
<211> LENGTH: 79
<212> TYPE: DNA
<213> ORGANISM: Artificial Sequence
<220> FEATURE:
<223> OTHER INFORMATION: Synthetically prepared oligonucleotide sequence

<400> SEQUENCE: 2
tttctgacgg caacttcaac tggggccggg ttgtcgccct tttctacttt gccagcaaac       60
tggtgctcaa ggccctgtg                                                   79

<210> SEQ ID NO 3
<211> LENGTH: 29
<212> TYPE: DNA
<213> ORGANISM: Artificial Sequence
<220> FEATURE:
<223> OTHER INFORMATION: Synthetically prepared oligonucleotide sequence

<400> SEQUENCE: 3 ggcataccccc tcgtagatgg gttagtttg                                       29

<210> SEQ ID NO 4
```

-continued

```
<211> LENGTH: 39
<212> TYPE: DNA
<213> ORGANISM: Artificial Sequence
<220> FEATURE:
<223> OTHER INFORMATION: Synthetically prepared oligonucleotide sequence

<400> SEQUENCE: 4
cacagggcct tgagcacccc catctacgag gggtatgcc                              39

<210> SEQ ID NO 5
<211> LENGTH: 21
<212> TYPE: DNA
<213> ORGANISM: Artificial Sequence
<220> FEATURE:
<223> OTHER INFORMATION: Synthetically prepared oligonucleotide sequence

<400> SEQUENCE: 5 ggcataccc tcgtagatgg g                                                  21

<210> SEQ ID NO 6
<211> LENGTH: 22
<212> TYPE: DNA
<213> ORGANISM: Artificial Sequence
<220> FEATURE:
<223> OTHER INFORMATION: Synthetically prepared oligonucleotide sequence

<400> SEQUENCE: 6
tttctgacgg caacttcaac tg                                                22

<210> SEQ ID NO 7
<211> LENGTH: 45
<212> TYPE: DNA
<213> ORGANISM: Artificial Sequence
<220> FEATURE:
<223> OTHER INFORMATION: Synthetically prepared oligonucleotide sequence
<220> FEATURE:
<221> NAME/KEY: misc_feature
<222> LOCATION: 43, 44, 45
<223> OTHER INFORMATION: n = 2'-O methyl uridine
<220> FEATURE:
<221> NAME/KEY: misc_feature
<222> LOCATION: 24
<223> OTHER INFORMATION: n = uridine
<220> FEATURE:
<221> NAME/KEY: misc_RNA
<222> LOCATION: (23)...(26)

<400> SEQUENCE: 7
agaggactat tacccgagga gtcngacggc aacttcaact ggnnn                       45

<210> SEQ ID NO 8
<211> LENGTH: 44
<212> TYPE: DNA
<213> ORGANISM: Artificial Sequence
<220> FEATURE:
<223> OTHER INFORMATION: Synthetically prepared oligonucleotide sequence

<400> SEQUENCE: 8
agtcctctct gacggcaact tcaactggag actcctcggg taat                        44

<210> SEQ ID NO 9
<211> LENGTH: 24
<212> TYPE: DNA
<213> ORGANISM: Artificial Sequence
<220> FEATURE:
<223> OTHER INFORMATION: Synthetically prepared oligonucleotide sequence
<220> FEATURE:
<221> NAME/KEY: misc_feature
<222> LOCATION: 22, 23, 24
```

<223> OTHER INFORMATION: n = 2'-O methyl uridine

<400> SEQUENCE: 9
ccagttgaag ttgccgtcag annn                                            24

<210> SEQ ID NO 10
<211> LENGTH: 76
<212> TYPE: DNA
<213> ORGANISM: Artificial Sequence
<220> FEATURE:
<223> OTHER INFORMATION: Synthetically prepared oligonucleotide sequence

<400> SEQUENCE: 10
tgcgacgacc gttgcgggca gtgatctcct tctgcatcct gtcgagtgat gtattcggtg      60
tcccagccgc agtgaa                                                     76

<210> SEQ ID NO 11
<211> LENGTH: 42
<212> TYPE: DNA
<213> ORGANISM: Artificial Sequence
<220> FEATURE:
<223> OTHER INFORMATION: Synthetically prepared oligonucleotide sequence

<400> SEQUENCE: 11
aggagctagt atcttgatct tcattgtgct gggtggcggt cg                        42

<210> SEQ ID NO 12
<211> LENGTH: 29
<212> TYPE: DNA
<213> ORGANISM: Artificial Sequence
<220> FEATURE:
<223> OTHER INFORMATION: Synthetically prepared oligonucleotide sequence

<400> SEQUENCE: 12
agtgatgtat tcggtgtccc agccgcagt                                       29

<210> SEQ ID NO 13
<211> LENGTH: 72
<212> TYPE: DNA
<213> ORGANISM: Artificial Sequence
<220> FEATURE:
<223> OTHER INFORMATION: Synthetically prepared oligonucleotide sequence

<400> SEQUENCE: 13
cgacaggatg cagaaggaga tcactgcccg cccacccagc acaatgaaga tcaagatact      60
agctcctaaa aa                                                         72

<210> SEQ ID NO 14
<211> LENGTH: 44
<212> TYPE: DNA
<213> ORGANISM: Artificial Sequence
<220> FEATURE:
<223> OTHER INFORMATION: Synthetically prepared oligonucleotide sequence

<400> SEQUENCE: 14
agtcctctct gacggcaact tcaactggag actcctcggg taat                      44

<210> SEQ ID NO 15
<211> LENGTH: 42
<212> TYPE: DNA
<213> ORGANISM: Artificial Sequence
<220> FEATURE:
<223> OTHER INFORMATION: Synthetically prepared oligonucleotide sequence
<220> FEATURE:
<221> NAME/KEY: misc_feature -continued

```
<222> LOCATION: 17
<223> OTHER INFORMATION: n = uridine
<220> FEATURE:
<221> NAME/KEY: misc_RNA
<222> LOCATION: (16)...(19)

<400> SEQUENCE: 15
tattacccga ggagtcngac ggcaacttca actggagagg ac                           42

<210> SEQ ID NO 16
<211> LENGTH: 24
<212> TYPE: DNA
<213> ORGANISM: Artificial Sequence
<220> FEATURE:
<223> OTHER INFORMATION: Synthetically prepared oligonucleotide sequence
<220> FEATURE:
<221> NAME/KEY: misc_feature
<222> LOCATION: 22, 23, 24
<223> OTHER INFORMATION: n = 2'-O methyl uridine

<400> SEQUENCE: 16
ccagttgaag ttgccgtcag annn                                              24
```